United States Patent
So et al.

(10) Patent No.: US 10,018,734 B2
(45) Date of Patent: Jul. 10, 2018

(54) DETECTOR PACK AND X-RAY CT APPARATUS

(71) Applicant: TOSHIBA MEDICAL SYSTEMS CORPORATION, Otawara-shi (JP)

(72) Inventors: Mayumi So, Kamakura (JP); Satoru Asagiri, Yokohama (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 172 days.

(21) Appl. No.: 15/057,339

(22) Filed: Mar. 1, 2016

(65) Prior Publication Data

US 2016/0259068 A1    Sep. 8, 2016

(30) Foreign Application Priority Data

Mar. 5, 2015 (JP) .................................. 2015-043924

(51) Int. Cl.
*A61B 6/00* (2006.01)
*G01T 1/20* (2006.01)
*A61B 6/03* (2006.01)

(52) U.S. Cl.
CPC .......... *G01T 1/2018* (2013.01); *A61B 6/4266* (2013.01); *A61B 6/032* (2013.01); *A61B 6/035* (2013.01); *A61B 6/4233* (2013.01)

(58) Field of Classification Search
CPC ...... G01T 1/2018; A61B 6/035; A61B 6/4266; A61B 6/032; A61B 6/4233
See application file for complete search history.

(56) References Cited

U.S. PATENT DOCUMENTS

2009/0314947 A1* 12/2009 Goushcha ............. G01T 1/2018
                                                    250/363.01
2014/0110592 A1*  4/2014 Nelson ................. G01T 1/1611
                                                    250/370.09

FOREIGN PATENT DOCUMENTS

| JP | 2001-215281 | 8/2001 |
| JP | 2007-47174 | 2/2007 |
| JP | 2008-246206 | 10/2008 |
| JP | 2011-191245 | 9/2011 |

* cited by examiner

*Primary Examiner* — Courtney Thomas
(74) *Attorney, Agent, or Firm* — Oblon, McClelland, Maier & Neustadt, L.L.P.

(57) ABSTRACT

According to an embodiment, a detector pack includes a first substrate, an X-ray detection unit, a second substrate, and a data acquisition device. The first substrate includes a first main surface and a second main surface. The X-ray detection unit is provided in the first main surface, converts an X-ray into an electrical signal, and outputs the electrical signal. The second substrate includes a third main surface and a fourth main surface and is disposed in a posture of making the third main surface face the second main surface. The data acquisition device is provided in at least any one of the third main surface and the fourth main surface.

8 Claims, 4 Drawing Sheets

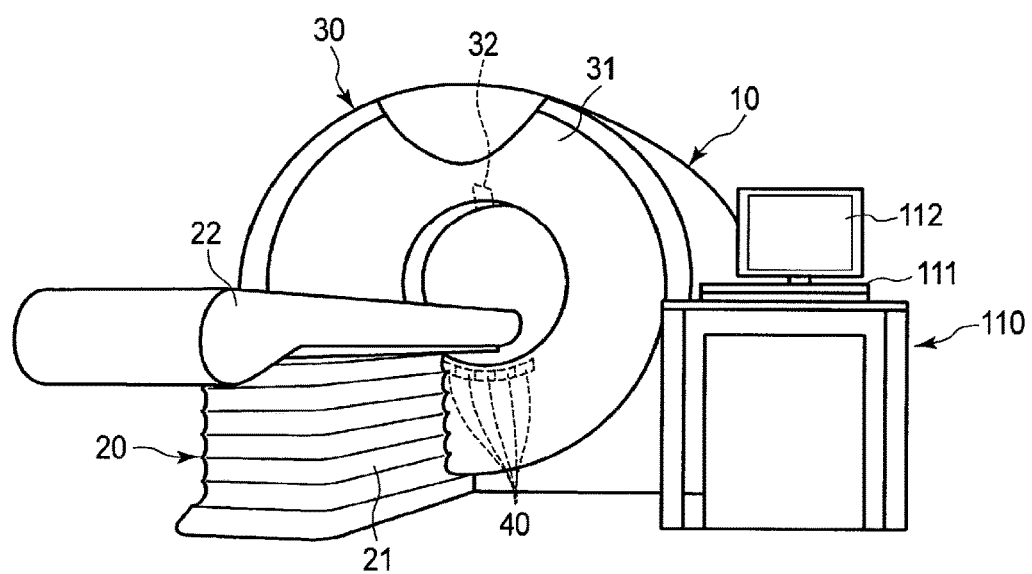
F I G. 1

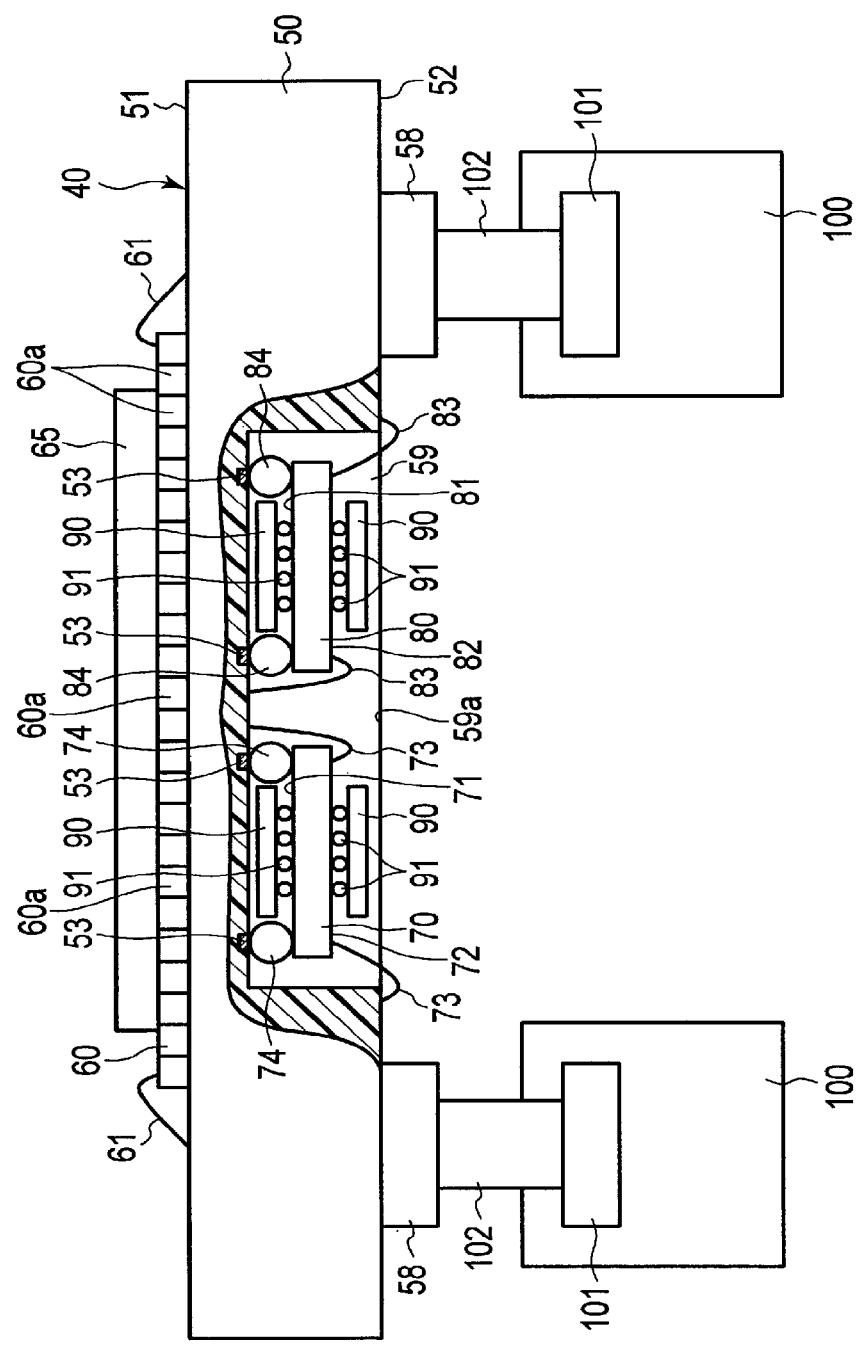
F I G. 4

DETECTOR PACK AND X-RAY CT APPARATUS

CROSS-REFERENCE TO RELATED APPLICATION

This application is based upon and claims the benefit of priority from Japanese Patent Application No. 2015-043924, filed Mar. 5, 2015; the entire contents of which are incorporated herein by reference.

FIELD

Embodiments described herein relate generally to a detector pack which detects a medical X-ray, and a medical X-ray CT apparatus which includes the detector pack.

BACKGROUND

A medical X-ray CT (Computed Tomography) apparatus (an X-ray laminography apparatus) includes a bed unit on which a subject lies, a circular gantry unit which can contain the bed unit, and a console unit which includes a monitor for displaying a state of the subject. The gantry unit includes an X-ray emitting unit which emits an X-ray toward the subject and a plurality of detector packs which detect the X-ray transmitting the subject. The detector packs are disposed in parallel in a rotation direction of the gantry unit.

The detector pack includes, for example, a first substrate made of a ceramic material, an optical semiconductor element which is provided on a first main surface of the first substrate, and a scintillator which is provided on the optical semiconductor element. In addition, the detector pack includes a second substrate which is electrically connected to the first substrate through a flexible substrate, an ASIC (Application Specific Integrated Circuit) which is provided on the second substrate, and an image processing device which is provided in the second substrate. The ASIC collects an electrical signal output by the optical semiconductor element, generates an electrical signal to be used in image processing based on the electrical signal, and outputs the electrical signal to be used in the image processing. The image processing device performs the image processing based on the electrical signal output by the ASIC.

On the other hand, the detector pack is requested for suppressing noises by shortening an electrical distance between the optical semiconductor element and the ASIC. As a structure for shortening the electrical distance between the optical semiconductor element and the ASIC, there is known a structure in which the ASIC is directly provided in a second main surface of the first substrate.

BRIEF DESCRIPTION OF THE DRAWINGS

FIG. 1 is a perspective view illustrating an X-ray CT apparatus according to an embodiment;

FIG. 4 is a side view illustrating a detector pack partially broken away according to a modification of the embodiment.

DETAILED DESCRIPTION

Figure 2:
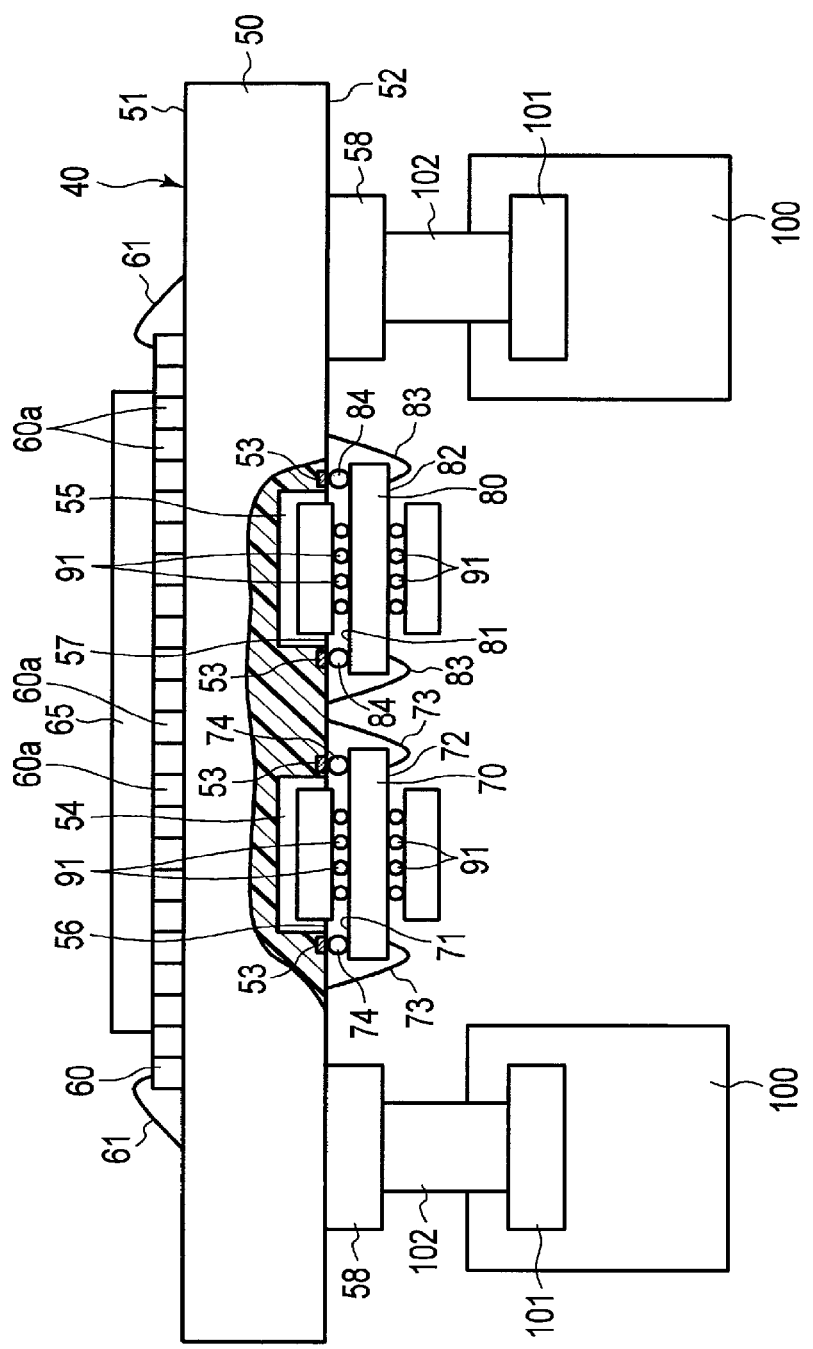
FIG. 2 is a side view illustrating a detector pack of the X-ray CT apparatus partially broken away.

According to an embodiment, a detector pack includes a first substrate, an X-ray detection unit, a second substrate, and a data acquisition device. The first substrate includes a first main surface and a second main surface. The X-ray detection unit is provided in the first main surface, is electrically connected to the first substrate, converts an X-ray into an electrical signal, and outputs the electrical signal. The second substrate includes a third main surface and a fourth main surface, is disposed in a posture of making the third main surface face the second main surface and is electrically connected to the first substrate. The data acquisition device is provided in at least any one of the third main surface and the fourth main surface to be electrically connected to the second substrate, collects the electrical signal output by the X-ray detection unit, generates a signal to be used in image processing based on the electrical signal, and outputs the generated signal.

An X-ray CT apparatus 10 according to the embodiment will be described using FIGS. 1, 2, 3, and 4. FIG. 1 is a perspective view illustrating the X-ray CT apparatus 10. As illustrated in FIG. 1, the X-ray CT apparatus 10 includes a bed unit 20 on which a subject can lie, a circular gantry unit 30 which emits the X-ray to the subject and can detect the X-ray transmitting the subject, and a console unit 110 which can control the bed unit 20 and the gantry unit 30.

The bed unit 20 includes a base portion 21 and a bed plate 22 which is provided on the base portion 21. The bed plate 22 is formed such that the subject can lie thereon. The bed plate 22 is formed to move with respect to the base portion 21 so as to be contained inside the gantry unit 30.

The gantry unit 30 includes a circular rotation portion 31, an X-ray emitting unit 32 which can emit the X-ray toward the inside of the rotation portion 31, and a plurality of detector packs 40 which can detect the X-ray emitted from the X-ray emitting unit 32. The rotation portion 31 is formed to be rotatable around its axis.

The detector packs 40 are fixed at positions facing the X-ray emitting unit 32 of the rotation portion 31. The detector packs 40 are arranged in a rotation direction of the rotation portion 31. FIG. 2 is a side view illustrating the detector pack 40 partially broken away.

As illustrated in FIG. 2, the detector pack 40 includes a substrate (the first substrate) 50 which includes a first main surface 51 and a second main surface 52, an optical semiconductor 60 which is provided on the first main surface 51 of the substrate 50, a scintillator 65 which is provided on the optical semiconductor 60, a first interposer (the second substrate) 70 which is disposed on a side near the second main surface 52 of the substrate 50 and includes a third main surface 71 and a fourth main surface 72, a second interposer (the second substrate) 80 which is disposed on a side near the second main surface 52 of the substrate 50 and includes a fifth main surface (the third main surface) 81 and a sixth main surface (the fourth main surface) 82, a plurality of ASICs 90 which are provided on both main surfaces of the interposers 70 and 80, and a pair of image processing devices 100.

The substrate 50 is, for example, a ceramic substrate made of a ceramic material. The substrate 50 includes a wiring 53. The second main surface 52 of the substrate 50 is formed with a first concave portion 54 and a second concave portion 55.

Figure 3:
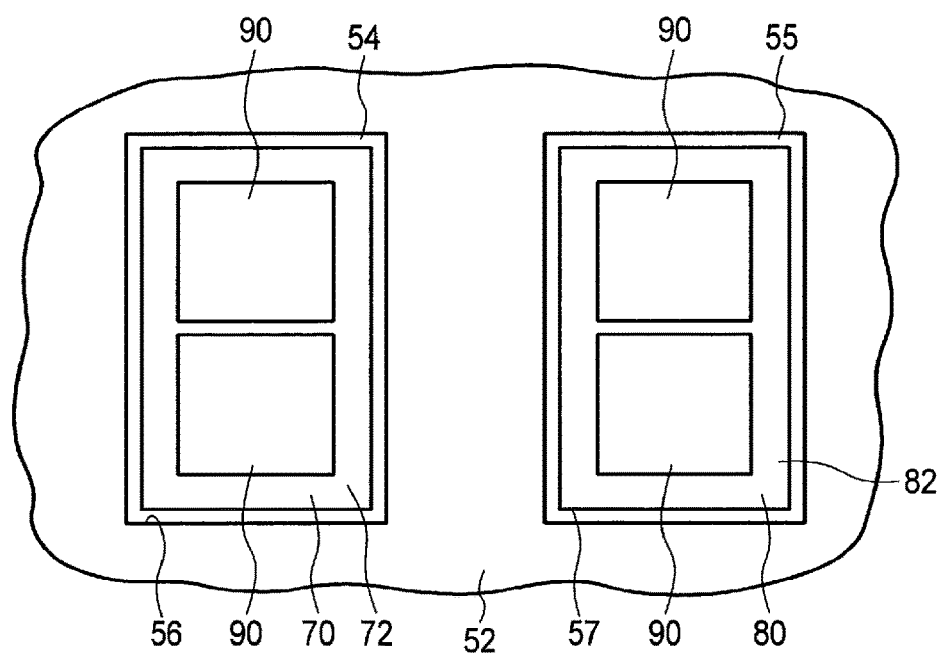
FIG. 3 is an enlarged view illustrating the center portion of a second main surface of a substrate of the detector pack.

The concave portions 54 and 55 are disposed in the vicinity of the center of the second main surface 52. FIG. 3 is an enlarged view illustrating the center portion of the second main surface 52. As illustrated in FIG. 3, an opening 56 of the first concave portion 54 is larger than the first interposer 70, and is formed in a size to make the first interposer 70 disposed therein. As illustrated in FIG. 2, the first concave portion 54 is formed in a depth to make a part of the ASIC 90 contained in a thickness direction of the substrate 50. As illustrated in FIG. 3, an opening 57 of the second concave portion 55 is larger than the second interposer 80, and is formed in a size to make the second interposer 80 disposed therein. As illustrated in FIG. 2, the second concave portion 55 is formed in a depth to make a part of the ASIC 90 contained in the thickness direction of the substrate 50.

An inter-first-substrate connector 58 is provided in each of both ends of the substrate 50. The inter-first-substrate connector 58 is electrically connected to the wiring 53 of the substrate 50.

The optical semiconductor 60 includes a plurality of optical semiconductor elements 60a. The optical semiconductor elements 60a are disposed in a matrix shape. The optical semiconductor element 60a converts the light into an electrical signal, and outputs the electrical signal. The optical semiconductor 60 is electrically connected to the wiring 53 of the substrate 50 using a wire 61 through a wire bonding method.

The scintillator 65 is mounted (disposed) in a matrix shape facing the optical semiconductor element 60a. The scintillator converts the X-ray into the light, and outputs the light.

The first interposer 70 is, for example, made of silicon. The first interposer 70 is disposed in a posture of making the third main surface 71 face the first concave portion 54 with a gap interposed with respect to the second main surface 52 of the substrate 50. The first interposer 70 is electrically connected to the wiring 53 of the substrate 50 using a wire 73 through a wire bonding method and using a bump 74 through a flip chip bonding method.

The second interposer 80 is disposed in a posture of making the fifth main surface 81 face the second concave portion 55 with a gap interposed with respect to the second main surface 52. The second interposer 80 is electrically connected to the wiring 53 of the substrate 50 using a wire 83 through a wire bonding method and using a bump 84 through a flip chip bonding method.

The ASIC 90 has a function of collecting the electrical signal output by the optical semiconductor element 60a to generate a signal to be used in the image processing based on the electrical signal, and outputting the signal to be used in the image processing.

A pair of ASICs (a first data acquisition device) 90 is provided on the third main surface 71 of the first interposer 70. As illustrated in FIG. 2, the ASIC 90 provided on the third main surface 71 is electrically connected to the wiring of the first interposer 70 using a bump 91 through a flip chip bonding method. The pair of ASICs 90 provided on the third main surface 71 is positioned inside the outer edge of the third main surface 71. Almost all the ASICs 90 provided in the third main surface 71 are contained in the first concave portion 54.

A pair of ASICs (a second data acquisition device) 90 is provided in the fourth main surface 72 of the first interposer 70. The ASIC 90 provided in the fourth main surface 72 is electrically connected to the wiring of the first interposer 70 using the bump 91 through a flip chip bonding method. The pair of ASICs 90 provided on the fourth main surface 72 is positioned inside the outer edge of the fourth main surface 72.

The arrangement direction of the pair of ASICs 90 provided in the third main surface 71 and the arrangement direction of the pair of ASICs 90 provided in the fourth main surface 72 are parallel to each other, and orthogonal to the arrangement direction of a pair of inter-first-substrate connectors 58.

The pair of ASICs (the first data acquisition device) 90 is provided in the fifth main surface 81 of the second interposer 80. The ASIC 90 provided in the fifth main surface 81 is electrically connected to the wiring of the second interposer 80 using the bump 91 through a flip chip bonding method. The pair of ASICs 90 provided on the fifth main surface 81 is positioned inside the outer edge of the fifth main surface 81. Almost all the ASICs 90 provided in the fifth main surface 81 are contained in the second concave portion 55.

The pair of ASICs (the second data acquisition device) 90 is provided in the sixth main surface 82 of the second interposer 80. As illustrated in FIG. 2, the ASIC 90 provided in the sixth main surface 82 is electrically connected to the wiring of the second interposer 80 using the bump 91 through a flip chip bonding method. The pair of ASICs 90 provided on the sixth main surface 82 is positioned inside the outer edge of the sixth main surface 82.

The arrangement direction of the pair of ASICs 90 provided in the fifth main surface 81 and the arrangement direction of the pair of ASICs 90 provided in the sixth main surface 82 are parallel to each other, and orthogonal to the arrangement direction of a pair of inter-first-substrate connectors 58.

The image processing device 100 is provided with an inter-second-substrate connector 101. The inter-second-substrate connector 101 is electrically connected to the image processing device 100. The inter-second-substrate connector 101 of the image processing device 100 is electrically connected to the inter-first-substrate connector 58 through a flexible substrate 102. The image processing device 100 is electrically connected to the wiring 53 of the substrate 50 through the flexible substrate 102.

The inter-second-substrate connector 101 of the other image processing device 100 is electrically connected to the other inter-first-substrate connector 58 through the flexible substrate 102. The other image processing device 100 is electrically connected to the wiring 53 of the substrate 50 through the flexible substrate 102.

Both of the image processing devices 100 receive the signal output by the ASIC 90, and can perform the image processing based on the received signal. Then, both of the image processing devices 100 can output image processed data.

The console unit 110 includes an input section 111 and a display section 112. The input section 111 is configured to receive an input such as operation information when an operator operates the bed unit 20 and the gantry unit 30. The console unit 110 can control the operation of the bed unit 20 and the operation of the gantry unit 30 based on the operation information input to the input section 111.

The display section 112 is configured to display an image based on the data output by both of the image processing devices 100. The image based on the data output by both of the image processing devices 100 is an image showing the inside of the subject generated based on the X-ray transmitting the subject.

Next, the operation of the X-ray CT apparatus 10 will be described. When the subject is laid on the bed plate 22 of the bed unit 20, the operator operates the input section 111 to start the operation of the X-ray CT apparatus 10. When the operation of the X-ray CT apparatus 10 is started, the bed plate 22 of the bed unit 20 moves into the gantry unit 30.

When the bed plate 22 moves into the gantry unit 30, the X-ray emitting unit 32 of the gantry unit 30 emits the X-ray.

The X-ray transmits the subject. Each detector pack 40 detects the X-ray transmitting the subject. Specifically, the X-ray transmitting the subject enters each scintillator 65. Each scintillator 65 receives the X-ray and generates the light.

Each optical semiconductor element 60*a* of the optical semiconductor 60 converts the light generated by the scintillator into an electrical signal. The optical semiconductor element 60*a* outputs the electrical signal. The electrical signals output from the optical semiconductor element 60*a* are transmitted to the ASIC 90 through the wiring 53 of the substrate 50 and the interposers 70 and 80.

The ASICs 90 collect the electrical signals output by the optical semiconductor elements 60*a* and generates a signal suitable to the image processing based on the electrical signal. In addition, the ASICs 90 output the generated signal. The signals output from the ASICs 90 are transmitted to both of the image processing devices 100 through the wiring 53 of the substrate 50 and the flexible substrate 102.

The image processing device 100 performs the image processing based on the signal generated by the ASIC 90. Both of the image processing devices 100 transmit the image processed data to the console unit 110.

The console unit 110 receives the data generated by both of the image processing devices 100. The display section 112 displays the image showing the inside of the subject generated based on the received data.

In the X-ray CT apparatus 10 configured as described above, the ASIC 90 can be disposed near the substrate 50 by using the interposers 70 and 80. Therefore, the distance from the optical semiconductor element 60*a* to the ASIC 90 can be shortened.

Since the distance from the optical semiconductor element 60*a* to the ASIC 90 can be shortened, the electric path where the electrical signal output by the optical semiconductor element 60*a* passes up to the ASIC 90 can be shortened. Therefore, it is possible to prevent noises from being generated.

Furthermore, since the ASICs 90 are provided in both main surfaces of the interposers 70 and 80, the ASICs 90 can be disposed in a stacking manner. Since the ASICs 90 can be disposed in a stacking manner, the detector pack 40 is not increased in size in a direction where the second main surface 52 is widened, and a lot of ASICs 90 can be provided.

In addition, the first concave portion 54 is formed in the second main surface 52, and almost all the ASICs 90 provided in the third main surface 71 of the first interposer 70 are contained in the first concave portion 54. Therefore, since a unit configured by the first interposer 70 and the ASICs 90 provided in both main surfaces can be disposed near the optical semiconductor element 60*a*, the distance from the optical semiconductor element 60*a* to the ASIC 90 provided in the first interposer 70 can be shortened.

In this way, since at least a portion of the ASIC 90 (provided in the third main surface 71 of the first interposer 70) on a side near the substrate 50 is contained in the first concave portion 54, the distance from the optical semiconductor element 60*a* to the ASIC 90 provided in the first interposer 70 can be shortened.

Similarly, the second concave portion 55 is formed in the second main surface 52, and a portion of the ASIC 90 provided in the fifth main surface 81 of the second interposer 80 is contained in the second concave portion 55. Therefore, since a unit configured by the second interposer 80 and the ASICs 90 provided on both main surfaces can be disposed near the optical semiconductor element 60*a*, the distance from the optical semiconductor element 60*a* to the ASIC 90 provided in the second interposer 80 can be shortened.

In this way, since at least a portion of the ASIC 90 (provided in the fifth main surface 81 of the second interposer 80) on a side near the substrate 50 is contained in the second concave portion 55, the distance from the optical semiconductor element 60*a* to the ASIC 90 provided in the second interposer 80 can be shortened.

In addition, since the ASICs 90 provided in the third main surface 71 of the first interposer 70 are contained in the first concave portion 54, and the ASICs 90 provided in the fifth main surface 81 of the second interposer 80 are contained in the second concave portion 55, a wide space can be secured on an opposite side of the unit of the first interposer 70 and the ASICs 90 and the unit of the second interposer 80 and the ASICs 90 from the substrate 50.

Therefore, the unit configured by the first interposer 70 and the ASICs 90 and the unit configured by the second interposer 80 and the ASICs 90 can be efficiently cooled using the space.

Further, since the space can be made widely, a cooling device may be disposed in the space to cool down the unit configured by the first interposer 70 and the ASICs 90 and the unit configured by the second interposer 80 and the ASICs 90.

Next, a modification of this embodiment will be described using FIG. 4. As illustrated in FIG. 4, a third concave portion 59 may be formed in the second main surface 52 of the substrate 50 instead of the concave portions 54 and 55. An opening 59*a* of the third concave portion 59 is formed in a size to contain the unit configured by the first interposer 70 and the ASICs 90 and the unit configured by the second interposer 80 and the ASICs 90.

Further, in this embodiment, the optical semiconductor 60 and the scintillator 65 configure an exemplary X-ray detection unit which converts the X-ray into the electrical signal and outputs the electrical signal. As another example, instead of the optical semiconductor 60 and the scintillator 65, an X-ray detection element which can directly convert the X-ray into the electrical signal may be used as the X-ray detection unit.

In addition, in this embodiment, the ASIC 90 is provided in the main surfaces 71 and 72 of the first interposer 70. As another example, the ASIC 90 may be provided in at least any one of the main surfaces 71 and 72. Similarly, the ASIC 90 is provided in the main surfaces 81 and 82 of the second interposer 80. As another example, the ASIC 90 may be provided in at least any one of the main surfaces 81 and 82.

While certain embodiments have been described, these embodiments have been presented by way of example only, and are not intended to limit the scope of the inventions. Indeed, the novel embodiments described herein may be embodied in a variety of other forms; furthermore, various omissions substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A detector pack comprising:
   a first substrate that comprises a first main surface and a second main surface;
   an X-ray detection unit that is provided in the first main surface, is electrically connected to the first substrate, converts an X-ray into an electrical signal, and outputs the electrical signal;

a second substrate that comprises a third main surface and a fourth main surface, is disposed in a posture of making the third main surface face the second main surface, and is electrically connected to the first substrate; and a plurality of data acquisition devices that are provided in the third main surface and the fourth main surface, electrically connected to the second substrate, collect the electrical signal output by the X-ray detection unit, and generate signals to be used in image processing based on the electrical signal, wherein a concave portion is formed in the second main surface of the first substrate, and at least a part of a unit is arranged in the concave portion, the unit being configured by the second substrate and the plurality of the data acquisition devices provided in the third main surface and the fourth main surface.

2. The detector pack according to claim 1,
wherein the X-ray detection unit comprises:
an optical semiconductor element that is provided in the first main surface, converts the light into an electrical signal, and outputs the electrical signal; and
a scintillator that is provided on the optical semiconductor element, converts an X-ray into the light, and outputs the light.

3. The detector pack according to claim 1, wherein
at least one other concave portion is formed in the second main surface of the first substrate, and
at least one other unit configured by the second substrate and the plurality of the data acquisition devices provided in the third main surface and the fourth main surface is at least partly arranged in said other concave portion.

4. The detector pack according to claim 1, further comprising
at least one other unit configured by the second substrate and the plurality of the data acquisition devices provided in the third main surface and the fourth main surface, at least a part of said at least one other unit being arranged in the concave portion.

5. An X-ray CT apparatus comprising:
an X-ray emitting unit that emits an X-ray; and
a plurality of detector packs, each of which comprises:
a first substrate that comprises a first main surface and a second main surface;
an X-ray detection unit that is provided in the first main surface, is electrically connected to the first substrate, converts an X-ray into an electrical signal, and outputs the electrical signal;
a second substrate that comprises a third main surface and a fourth main surface, is disposed in a posture of making the third main surface face the second main surface, and is electrically connected to the first substrate; and
a plurality of data acquisition devices that are provided in the third main surface and the fourth main surface, is electrically connected to the second substrate, collect the electrical signal output by the X-ray detection unit, generate signals to be used in image processing based on the electrical signal, and outputs the signal,
wherein a concave portion is formed in the second main surface of the first substrate, and
at least a part of a unit is arranged in the concave portion, the unit being configured by the second substrate and the plurality of the data acquisition devices provided in the third main surface and the fourth main surface.

6. The X-ray CT apparatus according to claim 5,
wherein the X-ray detection unit comprises:
an optical semiconductor element that is provided in the first main surface, converts the light into an electrical signal, and outputs the electrical signal; and
a scintillator that is provided on the optical semiconductor element, converts the X-ray into the light, and outputs the light.

7. The X-ray CT apparatus according to claim 5, wherein
at least one other concave portion is formed in the second main surface of the first substrate, and
at least one other unit configured by the second substrate and the plurality of the data acquisition devices provided in the third main surface and the fourth main surface is at least partly arranged in said other concave portion.

8. The X-ray CT apparatus according to claim 5, further comprising
at least one other unit configured by the second substrate and the plurality of the data acquisition devices provided in the third main surface and the fourth main surface, at least a part of said at least one other unit being arranged in the concave portion.

* * * * *